United States Patent
Fischer

(10) Patent No.: US 7,901,208 B2
(45) Date of Patent: Mar. 8, 2011

(54) CHEMICALLY IMPREGNATED ABSORBENT GINGIVAL RETRACTION CORD COMPRISING SILK

(75) Inventor: Dan E. Fischer, Sandy, UT (US)

(73) Assignee: Ultradent Products, Inc., South Jordan, UT (US)

( * ) Notice: Subject to any disclaimer, the term of this patent is extended or adjusted under 35 U.S.C. 154(b) by 0 days.

(21) Appl. No.: 11/551,542

(22) Filed: Oct. 20, 2006

(65) Prior Publication Data

US 2008/0096164 A1    Apr. 24, 2008

(51) Int. Cl.
*A61C 5/14* (2006.01)
(52) U.S. Cl. .......................................... 433/136
(58) Field of Classification Search ............... 433/136
See application file for complete search history.

(56) References Cited

U.S. PATENT DOCUMENTS

| | | | | |
|---|---|---|---|---|
| 4,321,038 A | * | 3/1982 | Porteous | 433/136 |
| 4,465,462 A | * | 8/1984 | Ticknor | 433/136 |
| 4,522,593 A | * | 6/1985 | Fischer | 433/136 |
| 4,617,950 A | * | 10/1986 | Porteous et al. | 132/321 |
| 4,728,291 A | | 3/1988 | Golub | 433/215 |
| 4,871,311 A | | 10/1989 | Hagne | |
| 4,892,482 A | * | 1/1990 | Lococo | 433/136 |
| 5,022,859 A | | 6/1991 | Oliva | |
| 5,540,588 A | | 7/1996 | Earle | |
| 5,558,652 A | * | 9/1996 | Henke | 604/529 |
| 5,676,543 A | | 10/1997 | Dragan | |
| 5,874,164 A | | 2/1999 | Caldwell | 428/306.6 |
| 5,899,694 A | | 5/1999 | Summer | |
| 6,179,872 B1 | | 1/2001 | Bell et al. | 623/11.11 |
| 6,375,461 B1 | | 4/2002 | Jensen et al. | |
| 6,455,030 B2 | | 9/2002 | Saito et al. | 424/49 |
| 6,612,839 B2 | | 9/2003 | Loynes | |
| 7,121,828 B2 | | 10/2006 | Fischer et al. | |
| 7,168,951 B2 | | 1/2007 | Fischer et al. | |
| 2002/0081550 A1 | | 6/2002 | Karazivan | |
| 2005/0277087 A1 | | 12/2005 | Fischer et al. | 433/136 |
| 2005/0277088 A1 | | 12/2005 | Fischer et al. | 433/136 |
| 2006/0060819 A1 | | 3/2006 | Jung | 252/186.38 |

(Continued)

FOREIGN PATENT DOCUMENTS

JP    1139057    5/1989

(Continued)

OTHER PUBLICATIONS

Braid. (n.d.). The American Heritage® Dictionary of the English Language, Fourth Edition. Retrieved Feb. 19, 2008, from Dictionary.com website: http://dictionary.reference.com/browse/braid.*

(Continued)

*Primary Examiner* — Cris L Rodriguez
*Assistant Examiner* — Heidi M Eide
(74) *Attorney, Agent, or Firm* — Workman Nydegger

(57) ABSTRACT

An absorbent and degradation resistant knitted gingival retraction cord comprising silk is formed from one or more strands by interlocking a plurality of loops. As a whole, the knitted retraction cord contains at least about 50% silk which, when manufactured so as to have a knitted structure, exhibits resistance to degradation and has the ability to absorb liquid (e.g., an active agent solution). An active agent is impregnated within the one or more strands and/or the plurality of interlocking loops of the knitted retraction cord such that the cord advantageously retains the active agent and resists degradation by the active agent.

15 Claims, 2 Drawing Sheets

U.S. PATENT DOCUMENTS

| | | | |
|---|---|---|---|
| 2007/0111160 | A1 | 5/2007 | Fischer et al. |
| 2008/0096164 | A1 | 4/2008 | Fischer |
| 2009/0098501 | A1 | 4/2009 | Klettke et al. |

FOREIGN PATENT DOCUMENTS

| | | |
|---|---|---|
| JP | 06056833 | 3/2006 |
| WO | 05122945 | 12/2005 |
| WO | WO2005/122945 | 12/2005 |

OTHER PUBLICATIONS

Goswami et al. Textile Yarns, Technology, Structure and Applications. New York: John Wiley and Sons 1997, pp. 26-27.*

Cotton retrieved from http:swicofil.com/products/001cotton.html.*

Selecting the Right Fiber for the Right Product by Kim Anderson. Retrieved from http://www.techexchange.com/thelibrary/selecting.html.*

History of Silk retrieved from http://weyouth.wordpress.com/2007/09/14/history-of-silk/.*

Fazekas, A., "Effects of Pre-Soaked Retraction Cords on the Microcirculation of the Human Gingival Margin" Oper Dent 27(4): 343-8 2002 (Abstract Attached).

Neito-Martinez, D., "Effects of Diameter, Chemical Impregnation and Hydration on the Tensile Strength of Gingival Retraction Cords" J. Oral Rehibil, 28(12): 1094-100 2002.

O'Mahony, A., "Effect of 3 Medicaments on the Dimensional Accuracy and Surface Detail Reproduction of Polyvinyl Siloxane Impressions" Quintessential Int., 31(3): 201-6 2001 (Abstract Attached).

Donovan, T.E., "Review and Survery of Medicaments Used With Gingival Retraction Cords" J. Prosthet Dent, 53(4):525-31 1985.

Office Action dated Feb. 8, 2006 cited in U.S. Appl. No. 11/064,725.

Office Action dated May 10, 2006 cited in U.S. Appl. No. 11/064,725.

Office Action dated Jul. 17, 2006 cited in U.S. Appl. No. 11/064,725.

NOA dated Dec. 1, 2006 cited in U.S. Appl. No. 11/064,725.

Office Action dated Feb. 8, 2006 cited in U.S. Appl. No. 10/863,974.

Office Action dated May 10, 2006 cited in U.S. Appl. No. 10/863,974.

NOA dated Jul. 20, 2006 cited in U.S. Appl. No. 10/863,974.

U.S. Appl. No. 12/135,756 titled "Chemically Pre-Impregnated Silk Retraction Cords Having Increased Strength" filed Jun. 9, 2008.

Office Action dated Aug. 14, 2009 cited in U.S. Appl. No. 11/622,844.

Office Action dated May 12, 2010 cited in U.S. Appl. 11/622,844.

Office Action dated Feb. 23, 2010 cited in U.S. Appl. No. 12/135,756.

Office Action dated Jun. 22, 2010 cited in U.S. Appl. No. 12/135,756.

Office Action dated Aug. 4, 2010 cited in U.S. Appl. No. 11/622,844.

Notice of Allowance dated Oct. 14, 2010 cited in U.S. Appl. No. 11/622,844.

* cited by examiner

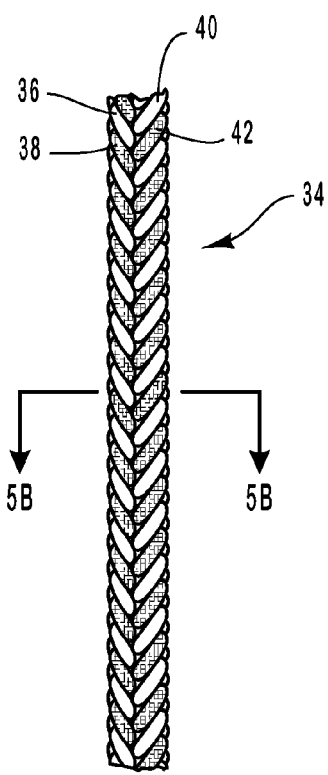
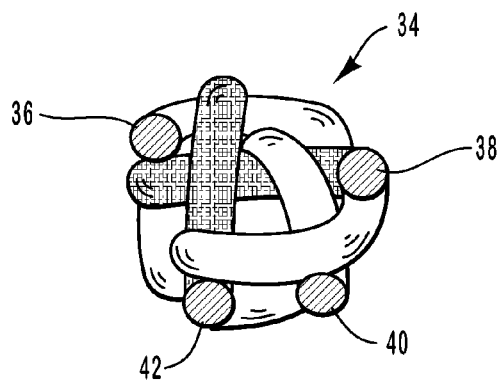
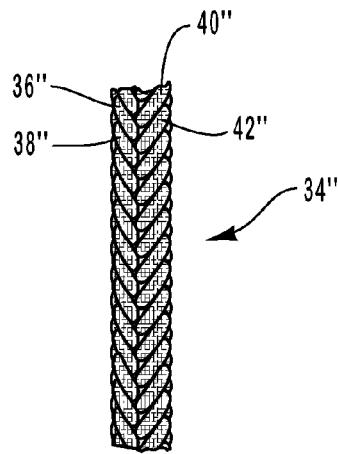
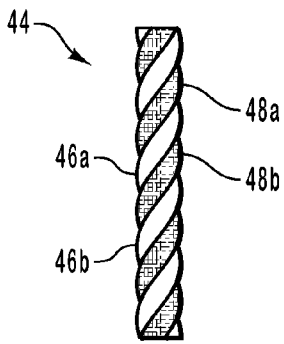
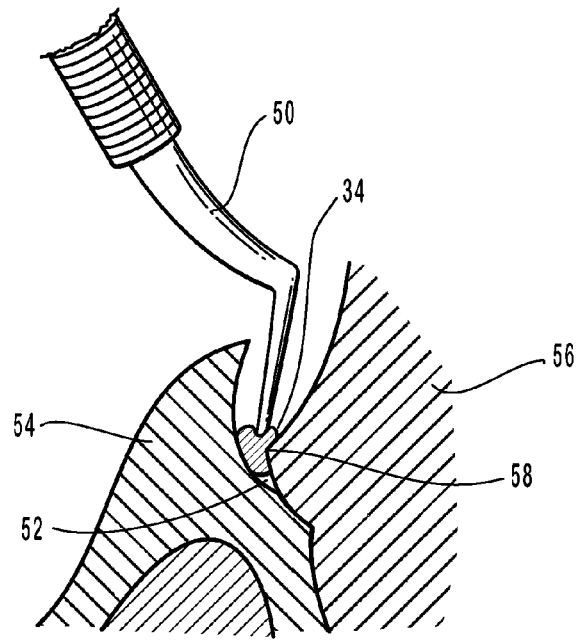
FIG. 5A FIG. 5B FIG. 6A FIG. 6B FIG. 7 FIG. 8

CHEMICALLY IMPREGNATED ABSORBENT GINGIVAL RETRACTION CORD COMPRISING SILK

BACKGROUND OF THE INVENTION

1. The Field of the Invention

The present invention relates to gingival retraction cords. More particularly, the present invention relates to chemically impregnated knitted retraction cords having high resistance to degradation and good absorption.

2. The Related Technology

When performing various dental procedures, it is often desirable to retract the gingival tissue to prepare the patient's teeth for the procedure. Taking dental impressions, placing crowns, performing bridge work, or effecting other dental restorations are examples of procedures that benefit from retracted gingival tissue. A widely used method for retracting gingival tissue involves the use of retraction cords which are typically braided or knitted for increased strength, flexibility and resilience. Examples of braided or knitted gingival retraction cords may be found in U.S. Pat. No. 4,321,038 to Porteous, U.S. Pat. No. 4,522,593 to Fischer, U.S. Pat. No. 4,617,950 to Porteous et al., U.S. Pat. No. 4,892,482 to Lococo and U.S. Publication No. 2005/0277087 to Fischer et al., herein incorporated by reference.

The most common purpose for using a retraction cord is to retract the gingiva away from the tooth to take an accurate and reliable impression of the tooth. It is critical to make an accurate impression of the tooth when constructing artificial crowns to ensure that the crown remains properly secured to the tooth for an extended period of time. It is particularly important to make an accurate impression of the tooth in the area at or below the gingival margin. Failure to take an accurate impression can result in a poorly-formed or deficient prosthesis, particularly at the gingival margin. Premature failure of a crown is often due to poor marginal detail in the impression used to fabricate the crown.

The person's gingiva, or "gums", not only prevents an accurate impression of the proper shape of a person's tooth beneath the gingiva, it may also bleed if torn or damaged by high speed cutting drills or burrs used to remove tooth material preparatory to placing a crown. This bleeding may further interfere with the taking of a good impression because extravasated blood tends to prevent adequate cleaning and drying of the marginal area of the tooth prior to taking an impression and tends to displace the impression material before it can set. Thus, the dual problems of contraction of the gingival cuff and the presence of hemorrhaging tissues make it impractical to simply take an impression following shaping of the tooth with a high speed drill or burr without retraction of the gingiva.

To control or inhibit the tendency of the gingiva to bleed when physically retracted by the retraction cord and/or if accidentally cut or nicked by the high speed drill or burr, retraction cords are often treated with a hemostatic agent. One type of hemostatic agent includes astringents, which lock or seal off exposed blood vessels so as to arrest bleeding. U.S. Pat. Nos. 4,321,038, 4,522, 593, 4,617,950 and 4,892,482, referred to above, discuss the use of astringents such as potassium aluminum sulfate, also known as "alum".

Many chemicals used to impregnate a retraction cord can have an adverse affect on the strength and integrity of the fibers in the retraction cord. Many retraction cords are made of knitted or braided cotton fibers, which are absorbent so as to retain the active agent within the cotton fibers. However, the use of a hemostatic agent in the retraction cord can degrade the cord over time, making it more likely to fray and/or fail during use. If fibers in the knit or braid fail during use, the dental packing instrument used to insert the retraction cord into the sulcus can slip through the fibers and potentially cut or injure the underlying tissue. In addition, fragments of the retraction cord can remain embedded between the tooth and gums, providing greater risk of infection. Frayed filaments can easily lodge within coagulum, which can be painful to the patient and result in a recurrence of bleeding when the cord is removed. Furthermore, the expandability and resilience of the retraction cord diminishes as the integrity of the knit or weave of the cord degrades.

Therefore, it would be an improvement in the art to provide a gingival retraction cord that is absorbent so as to retain an active agent (e.g., a hemostat solution), and which also resists decomposition and degradation due to a hemostatic or other corrosive agent. It would be a further improvement if such a retraction cord could be formed from strands comprising a single material while maintaining desired properties of being absorbent yet resistant to corrosive dental materials.

BRIEF SUMMARY OF THE INVENTION

The present invention is directed to a gingival retraction cord that resists degradation when impregnated with an active agent (e.g., a hemostatic agent). The retraction cord is formed from one or more strands by interlocking a plurality of loops so as to form a knitted retraction cord that is deformable and moisture absorbent. Advantageously, the one or more strands (as a whole) comprise at least about 50% silk, which material the inventors have discovered exhibits resistance to degradation while also exhibiting the ability to absorb liquid (e.g., a hemostatic agent solution) when manufactured so as to have a knitted structure. An active agent is impregnated within the one or more strands and/or the plurality of interlocking loops of the knitted retraction cord such that the cord advantageously retains the active agent and resists degradation by the active agent. Such an outcome is surprising, as silk has been typically regarded as a non-absorbent material. In addition, as a class, natural fibers (of which silk is one) have typically been regarded as subject to degradation when exposed to hemostatic agents or other corrosive materials.

In one embodiment, each strand may comprise at least about 50% silk. In another embodiment, one or more strands of a single material may be used, so long as at least about 50% of the overall knitted retraction cord comprises silk. Cotton and/or other absorbent materials (e.g., natural fibers) may be included as desired. Synthetic degradation-resistant fibers (e.g., nylon and/or polyester) may also be included as desired. Absorbent materials may be present to provide increased absorption to the cord, while synthetic degradation resistant materials may provide additional structural integrity for resisting degradation caused by the one or more active agents.

In an embodiment where the retraction cord is formed from one or more strands of blended fibers, the various fibers (i.e., silk and otherwise) may be twisted together to form one or more blended strands. The blended strands may then be knitted to form the retraction cord of the present invention. In one such embodiment, each strand of the knit can advantageously include silk fibers such that the entire knit resists degradation. The blended strands can also be knitted together with 100% silk strands, blended strands having a higher silk content, blended strands having a lower silk content, or strands having no silk.

The silk fibers within the cord give the retraction cord durability and integrity in the presence of the active agent. Even if the active agent breaks down or otherwise weakens cotton and/or other degradable natural strands or fibers, the degradation resistant silk strands and/or fibers resist such degradation, thereby preserving the overall structural integrity of the knit.

The silk and any other strands and/or fibers used to make the retraction cord of the present invention are blended together such that each fiber and strand follows the knit pattern. In this way, any blending of materials does not compromise the beneficial features of the knit pattern. Rather, the knitted retraction cord is advantageously elastic and resilient in both the longitudinal and transverse dimensions.

In a particularly preferred embodiment, the retraction cord is formed from one or more strands wherein each strand consists essentially of silk. In an embodiment where each strand consists entirely of silk, manufacture is simplified, as only one strand material is required while also providing beneficial characteristics of absorbency and degradation resistance.

These and other features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only typical embodiments of the invention and are therefore not to be considered limiting of its scope. The invention will be described and explained with additional specificity and detail through the use of the accompanying drawings in which:

FIG. 5A illustrates a length of knitted retraction cord formed from four strands according to an exemplary embodiment of the present invention, in which two strands are made from silk;

FIG. 5B illustrates a transverse cross-section of the knitted retraction cord of FIG. 5A taken along line 5B-5B;

FIG. 6A illustrates a length of knitted retraction cord formed from four strands according to an exemplary embodiment of the present invention, in which three strands are made from silk;

FIG. 6B illustrates a length of knitted retraction cord formed from four strands according to an exemplary embodiment of the present invention, in which all four strands are made from silk;

FIG. 7 illustrates an alternative embodiment of the present invention showing a single strand of the knit being made from a blend of silk and other fibers; and FIG. 8 schematically illustrates a cross-sectional portion of a tooth, the tooth's associated gingival cuff, and a knitted retraction cord being packed into the gingival sulcus between the tooth and the gingival cuff.

DETAILED DESCRIPTION OF EXEMPLARY EMBODIMENTS

I. Definitions and Introduction

As used herein, the terms "knitting" and "knitted" relate to a process of using one or more separate strands to form a series of interlocking loops. A "strand" may include one or more fibers which are twisted or otherwise joined together.

As used herein, the term "silk" refers to protein animal fibers produced by various insects (e.g., the silkworm larvae).

The present invention is directed to gingival retraction cords that are formed of a material and in a manner that yields a cord that is both resistant to degradation and absorbent so as to allow impregnation with an active agent (e.g. a hemostatic agent). The retraction cord is formed from one or more strands by interlocking a plurality of loops so as to form a knitted retraction cord that is deformable and moisture absorbent. The strand material (as a whole) comprises at least about 50% silk, preferably at least about 80% silk, more preferably at least about 90% silk, and most preferably at least about 95% silk. In one embodiment, the entirety of the strands are formed of silk.

The inventors have discovered that silk-containing strands, when knitted, exhibit both resistance to degradation and the ability to absorb liquid (e.g., a hemostatic agent solution). Silk has traditionally been regarded as a non-absorbent material in the context of retraction cords, but because of a synergistic interaction between the silk material and the knitted structure, the liquid is absorbed within the one or more strands and/or the plurality of interlocking loops of the knitted structure. It is for this reason that at least about 50% (and preferably much more) of the strand material comprises silk. The result is a knitted gingival retraction cord that may advantageously be formed of a single material (i.e., silk), while exhibiting both resistance to degradation and absorption so as to retain an active agent.

II. Exemplary Knitted Retraction Cords

A. Knit Patterns

Figure 1:
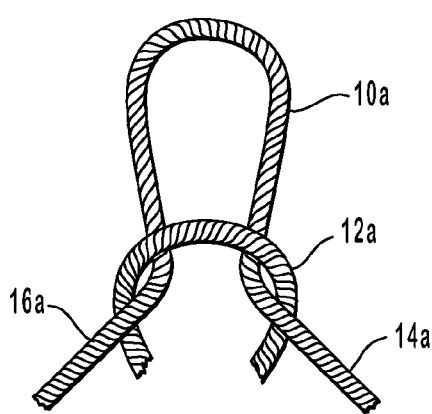
FIG. 1 illustrates an open-loop configuration used in knitting.
Figure 2:
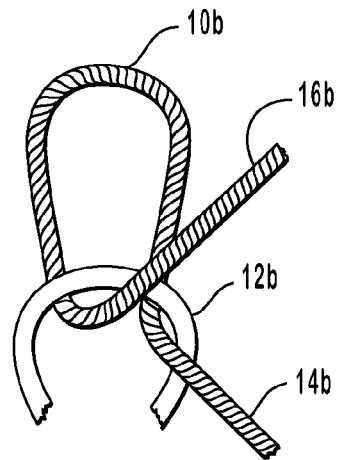
FIG. 2 illustrates a closed-loop configuration used in knitting.

FIGS. 1 and 2 illustrate two exemplary types of knitting techniques that may be used to form the retraction cords of the present invention. FIG. 1 illustrates an "open" loop, while FIG. 2 illustrates a "closed" loop. The "open" loop shown in FIG. 1 is formed using a first loop 10a that is interlocked with an adjacent loop 12a such that ends 14a and 16a of loop 10a do not cross one another. In contrast, FIG. 2 illustrates what is generally known as a "closed" loop knit in which end 16b of first loop 10b bends back over and crosses in a manner that closes off loop 10b.

Figure 3:
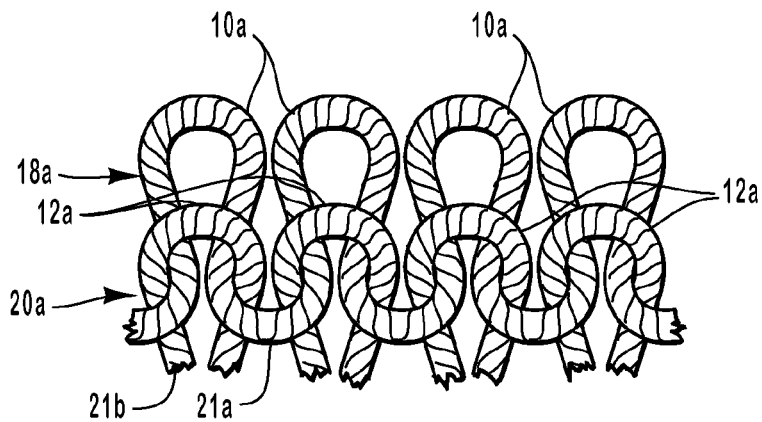
FIG. 3 illustrates an exemplary manner in which one or more strands can be knitted using the open-loop configuration of FIG. 1 so as to form a knitted retraction cord.

FIG. 3 illustrates two rows (generally designated 18a and 20a) of interlocked loops constructed with the open-loop configuration shown in FIG. 1. As seen in FIG. 3, row 18a includes a plurality of loops 10a, which are interlocked with loops 12a of adjacent row 20a. FIG. 3 illustrates "weft" knitting, which is made from one loop to the next in the same course (i.e., row), of loops, and which can be done using a first strand 21a for row 18a and a second strand 21b for row 20a. Alternatively, weft knitting can be performed using a single strand or more than two strands.

As discussed more fully below, strands 21a and 21b may include a blend of different materials, or one or both may be formed entirely of silk. In any case, at least about 50% of the overall strand material is formed of silk so as to make the knitted retraction cord resistant to the degrading effects of a hemostatic or other active agent, while also being absorbent so as to allow impregnation by the active agent. Absorbent fibers (e.g., cotton) may be incorporated into one or more of the strands to yield increased absorbency, while synthetic degradation resistant fibers (e.g., polyester and/or nylon) may be incorporated into one or more of the strands to provide resistance to degradation. While synthetic degradation resistant fibers may be included, silk is particularly preferred over synthetic degradation resistant fibers because silk is degradation resistant and there is advantageously a synergistic effect associated with the combination of silk fibers and the knitted structure, resulting in an absorbent knit structure which is not characteristic of synthetic fibers, even in a knit structure. For this reason, if present, synthetic degradation resistant fibers (e.g., nylon and/or polyester) are preferably included in a fraction no greater than about 25% of the overall strand materials.

Figure 4:
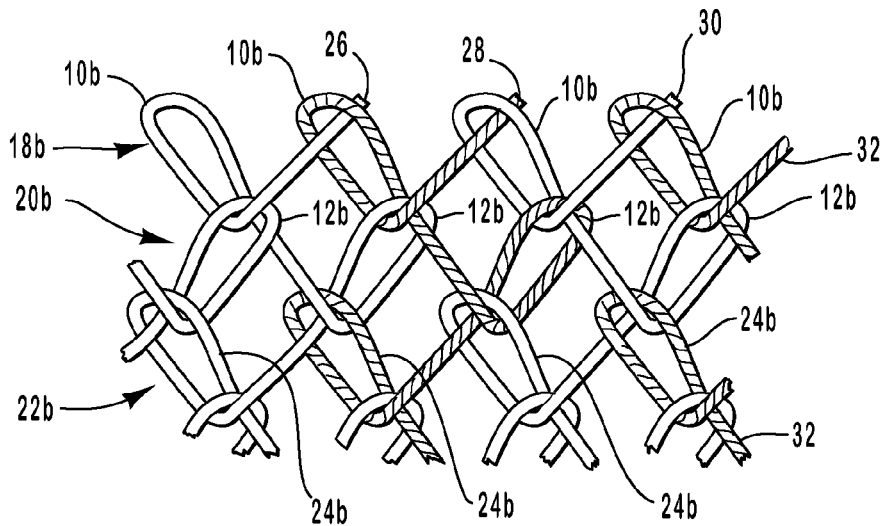
FIG. 4 illustrates an exemplary manner in which one or more strands may be interlocked and knitted using the closed-loop configuration of FIG. 2 so as to form a knitted retraction cord.

FIG. 4 illustrates three rows (generally designated at 18b, 20b, and 22b, respectively) of interlocked loops constructed utilizing the closed-loop configuration of FIG. 2. As seen in FIG. 4, row 18b includes loops 10b, which are interlocked with the loops 12b of adjacent row 20b. Loops 12b of row 20b are in turn interlocked with the loops 24b of adjacent row 22b, and so on.

FIG. 4 illustrates "warp" knitting in which several strands 26, 28, 30, and 32, are interconnected such that the interlocking loops of each strand connect from one row to the next. At least 50% of the overall strand material comprises silk. Each strand may comprise a single material, or one or more of the strands may comprise a blend of materials. In any case, at least about 50% of the material from which strands 26, 28, 30, and 32 are formed comprises silk so as to make the knitted retraction cord resistant to the degrading effects of a hemostatic agent, while also being absorbent. Absorbent fibers and/or strands (e.g., cotton) may be incorporated into one or more of the strands of the knit structure to yield increased absorbency, while synthetic degradation resistant fibers may be incorporated into one or more of the strands or the knit structure to provide additional resistance to degradation. While synthetic degradation resistant fibers and/or strands (e.g., nylon and/or polyester) may be included, silk is particularly preferred over synthetic degradation resistant fibers and/or strands because silk is degradation resistant and advantageously exhibits a synergistic effect associated with the combination of silk fibers and the knitted structure, resulting in an absorbent knit structure which is not characteristic of synthetic fibers and/or strands, even in a knit structure. In other words, a knit retraction cord formed entirely of synthetic degradation resistant fibers does not exhibit the absorbency that a knit retraction cord formed entirely of silk does. For this reason, if present, synthetic degradation resistant fibers and/or strands (e.g., nylon and/or polyester) are preferably included in a fraction no greater than about 25% of the overall fiber and/or strand materials. In one embodiment, the knit retraction cord is substantially devoid of synthetic degradation resistant fibers.

FIG. 5A shows a gingival retraction cord 34 knitted from four strands 36, 38, 40, and 42 using the closed-loop pattern shown in FIGS. 2 and 4. The number and pattern of strands 36, 38, 40, and 42 is more readily apparent in the cross sectional view of retraction cord 34 illustrated in FIG. 5B. In FIG. 5A, two of the four strands (i.e., strands 38 and 42) comprise silk, while strands 36 and 40 may comprise another material (e.g., cotton, nylon, and/or polyester). In FIG. 6A, three of the four strands (i.e., 38', 40', and 42') of cord 34' comprise silk, while strand 36' may comprise another material. In FIG. 6B, all four strands 36", 38", 40", and 42" of cord 34" are comprised entirely of silk.

It will be appreciated that the knitted retraction cord of the present invention can be constructed using either an open-loop or a closed-loop pattern or structure, as shown in FIGS. 1-4. Retraction cords 34, 34' or 34" can also be made using other kitting patterns so long as the knit pattern forms a plurality of interlocking loops, which provide elasticity and/or resilience, while also providing absorbency and degradation resistance when the cord is made from at least about 50% silk. Furthermore, those skilled in the art will recognize that the knit pattern can include any number of strands and each strand can be made from any number of fibers.

B. Blends of Strands and/or Fibers

With continued reference to FIGS. 5A and 5B, strands 36, 38, 40, and 42 represent a plurality of strand materials. In an exemplary embodiment, strands 38 and 42 are silk strands, while strands 36 and 40 may be cotton. The different strands are knitted to form retraction cord 34 having a 2:2 ratio of silk to other strands. By way of further example, in FIG. 6A, three of the four strands (i.e., 38', 40', and 42') are silk. The blended strands are knitted to form retraction cord 34' having a 3:1 ratio of silk to other strands. The ratio may be adjusted as desired by using more or fewer silk and/or other strands. In FIG. 6B, all four of the strands are silk. Such a configuration advantageously only requires a single material (i.e., silk) in the manufacture of the knitted retraction cord, while also providing degradation resistance and absorption.

In one embodiment, a cord comprising silk and at least one other material is created by blending two or more fibers to make a strand. One or more strands (whether of a single material or formed of a blend of fibers) are then knitted to make a retraction cord. FIG. 7 illustrates an exemplary strand 44 that is made from a blend of silk fibers 46a and 46b and other material (e.g., cotton) fibers 48a and 48b. Fibers 46a, 46b, 48a, and 48b are twisted together to form strand 44 having a 2:2 ratio of silk to other fibers. It will be understood that the ratio of strand 44 may be adjusted as desired by using more or fewer silk and/or other fibers. It will be understood that more or fewer than four fibers may be used to form a desired strand.

It will be appreciated that strands can be made from more or fewer silk and/or other fibers and that the knitted retraction cords of the present invention can have almost any desired blend ratio of silk to other materials that is at least about 50% silk (i.e., at least about a 1:1 ratio of silk to other fibers). Furthermore, blended strands may also be knitted with other blended or non-blended strands to create a retraction cord that may incorporate materials in addition to silk.

Materials in addition to silk that may be used to create the blends employed with the present invention include natural and synthetic polymers, coated polymers, metal filaments, or any other threadable material that can give the retraction cord a desired property. For instance, cotton may be used for its excellent absorbency and biocompatibility. Synthetic materials (e.g., nylon and/or polyester) may be used to provide additional degradation resistant strands that are not silk. Cotton, nylon, and/or polyester may also be included to reduce the cost of the cord as compared to pure silk. In one embodiment a polymer fiber or metal filament can be included to give the retraction cord a desired resiliency, elasticity, or deformability. A metal filament such as silver can also be included to make the retraction cord radioopaque.

A significant fraction of silk fiber (i.e., at least about 50%) is included in the knit of the retraction cord to resist degradation by an active agent and provide absorbency. As further discussed below, active agents such as hemostatic agents are advantageously included in the retraction cord to assist in controlling gingival bleeding during a procedure. Typically, active agents break down absorbent fibers such as cotton. While polyester and/or nylon fibers do resist degradation, they are not absorbent. The inclusion of silk in the knit results in a retraction cord that is absorbent and resists degradation. Degradation leads to failure of the retraction cord and/or fraying in which the frayed filaments easily lodge within and bond to clotting blood, which can result in a recurrence of bleeding and pain for the patient upon removal. Preventing the failure of the knit helps ensure that the retraction cord properly retracts gingival tissue and reduces the chances that a packing instrument will pierce the knit of the cord and damage the underlying tissue.

As mentioned above, the silk and optionally an additional synthetic non-degrading material (e.g., polyester and/or nylon) may be blended into the knit through a strand or through individual fibers that form part of a strand. In this regard, it can be advantageous to include silk and/or a synthetic non-degrading material as a fiber in each strand of the knit. In this manner, each strand is structurally supported and improved by the presence of silk and/or synthetic fibers.

C. Elasticity and Resilience

The knitted retraction cords (i.e., 34, 34', 34") of FIGS. 5A-6B are characteristically highly elastic and resilient in both the longitudinal and transverse dimensions. Each of the strands (e.g., strands 36, 38, 40, and 42 of cord 34) used to create the blended cord may be formed as part of the knit of each retraction cord so as to not disrupt the advantages provided by a knit pattern.

Cords 34, 34', and 34" can be easily stretched along their length, and squeezed or compressed radially because of the properties of the knit pattern. In a knitted cord, the strand or strands are oriented so that a portion of each strand runs transversely, or at approximately right angles to the longitudinal axis of the cord, thus making the cord more compressible and also more stretchable along its length. In contrast, a twisted-strand or braided-type cord has very little longitudinal or transverse elasticity.

In general, as between twisted-strand or braided-type cords, the use of braided retraction cords has been found to be advantageous over twisted-strand cords because the braided cord better maintains its structural integrity under the force of the dental packing instrument and under the pressure exerted by the surrounding gingival tissue once the cord has been packed into the sulcus.

Surprisingly, the use of a resilient knitted retraction cord has also been found to be more advantageous still in retracting gingival tissue, despite the fact that its inherent elasticity and resilience might be thought to be detrimental by those who have used braided or twisted-strand retraction cords.

Longitudinal elasticity, or the ability to stretch the retraction cord lengthwise, is beneficial because it avoids the tendency for the packed cord to be dislodged as additional cord is pushed into the sulcus between the tooth and the gingival cuff. As the retraction cord is packed, the "stretch" in the knitted cord permits stress to be placed on the cord without causing already packed portions of the cord to be pulled out of the sulcus.

D. Active Agents and Absorbency

The retraction cord is advantageously absorbent so as to allow an active agent to be impregnated within one or more strands and/or within the plurality of interlocking loops of the knitted retraction cord. Hemostatic agents, including astringents and/or other vasoconstrictors, can be impregnated in the retraction cord to control bleeding and/or stiffen gingival tissue.

Active agents that may be useful in assisting hemostasis include, but are not limited to aluminum compounds such as potassium aluminum sulfate, aluminum ammonium sulfate, aluminum sulfate, aluminum chlorohydrate, aluminum acetate, aluminum chloride, other water soluble astringent aluminum salts, and mixtures thereof. Another class of astringents includes iron-based compounds such as ferric salts, including but not limited to ferric sulfate, ferric subsulfate, ferric chloride, and mixtures thereof. Other astringents include permanganates, tannins and zinc chloride. In one embodiment the active agent may comprise a vasoconstrictor such as epinephrine and/or propylhexedrine.

The active agent is typically delivered to the gingival tissue in a solution, such as an aqueous solution. As discussed above, the retraction cord comprising silk is advantageously absorbent. The solution is absorbed within the silk fibers, strands, within any additional absorptive material (e.g., cotton) that may optionally be included, and/or within the plurality of interlocking loops of the knit structure. While the active agent may be impregnated using a mechanism other than a solution, a solution is beneficial because it can easily be expressed in the sulcus.

The ability of knitted retraction cords to effectively deliver the active agents to the gingival tissue is greatly augmented by the fact that the knitted retraction cords are compressed when packed in the sulcus. Thus, knitted cords may actually express the hemostatic or other agents into the small capillaries of the gingival tissue when compressed, thereby forcing the active agents into the bleeding pores so as to stop hemorrhage.

The knitted pattern of retraction cords 34, 34', and 34" advantageously helps absorb and deliver the active agent. The interlocking loops of the knit pattern substantially increase the interstitial volume of the knitted retraction cords, which allows the retraction cords to carry larger amounts of active agent as compared to twisted or braided cords, all else being equal. For example, the inventor has discovered that knitted retraction cords retain up to about 250% more liquid volume than a braided cord of the same material. Because the knit pattern carries additional active agent, silk, a degradation resistant, relatively non-absorbent material can advantageously be used within the knit pattern, and the resulting retraction cord is both degradation resistant and absorptive.

III. Exemplary Methods of Use

FIG. 8 shows a dental instrument 50 being used to press the gingival retraction cord 34 within the sulcus 52 between the gingival cuff 54 and the tooth 56. The resilience and flexibility in the transverse direction allows the knitted retraction cord 34 to conform to irregularities, such as a margin 58 of tooth 56.

Even if the loops of the knitted retraction cord are left rather loose, because of the intricate interlocking network, there is little or no tendency for the dental packing instrument to slip through the retraction cord. Rather, the compressibility of the knitted cord 34 causes the cord 34 to "dimple" around the edges of the dental packing instrument 50.

Because of the compressibility and bendability of the knitted retraction cords there is less tendency for the cords to damage underlying gingival tissue as force is applied during packing. This is because the force of the packing instrument tends to be spread out over a larger area by the interlocking loops of the knitted cord. Also, the transverse resilience of the knitted cord enables it to conform to irregularities within the sulcus. Thus, the knitted cord can accomplish both horizontal and vertical retraction using a single cord.

Another advantage of knitted retraction cords is their tendency to return to their original, uncompressed shape because of their resilience. Thus, when a knitted retraction cord is packed into the sulcus, it is compressed, and the "memory" in the retraction cord causes the cord to gently push outward against the gingival tissue 54. This outward pushing increases the ability of the knitted cord 34 to retract gingival tissues over braided and/or twisted retraction cords.

Another advantage arising from the compressibility of knitted retraction cords is realized when retracting gingival tissue around the front teeth. The labial gingival tissue is particularly thin and membranous as compared to the lingual gingival tissue. Using the knitted retraction cords of the present invention, the lingual gingival tissue can be adequately retracted with the knitted retraction cord only slightly compressed, and by virtue of its compressibility and its ability to stretch and become thinner, the same cord can be packed into the sulcus on the labial side of an interior tooth without over-retracting the gingival tissue. The cord then exerts a general, steady outward force on the tissue, which advantageously retracts the tissue without causing any undue damage to the thin, sensitive labial gingival tissue.

The retraction cord may be chemically impregnated with an active agent over an extended period of time without compromising the knit pattern and the benefits that accompany a knitted cord. The silk fibers, strands, and interlocking loops of the retraction cord permit chemical impregnation yet give the retraction cord strength in the event that the active agent degrades any optional degradable fibers (e.g., cotton) in the cord.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A chemically impregnated liquid absorbent gingival retraction cord that is resistant to degradation by corrosive agents, comprising:
   a liquid absorbent knitted retraction cord formed from one or more silk-containing strands, the one or more strands being formed into a knit of a plurality of interlocking loops so as to form the knitted retraction cord and so as to be deformable and liquid absorbent, wherein the retraction cord is comprised of silk; and
   a corrosive active agent impregnated within the liquid absorbent knitted retraction cord,
   wherein the knitted retraction cord is liquid absorbent and the silk resists degradation by the corrosive active agent.

2. A chemically impregnated liquid absorbent gingival retraction cord as defined in claim 1, wherein the retraction cord is substantially free of synthetic fibers and consists essentially of natural fibers.

3. A chemically impregnated liquid absorbent gingival retraction cord as defined in claim 1, wherein the corrosive active agent is a hemostat selected from the group consisting of potassium aluminum sulfate, aluminum ammonium sulfate, aluminum sulfate, aluminum chlorohydrate, aluminum acetate, aluminum chloride, ferric sulfate, ferric subsulfate, ferric chloride, permanganates, tannins, zinc chloride, and combinations thereof.

4. A chemically impregnated liquid absorbent gingival retraction cord as defined in claim 1, further comprising a vasoconstrictor selected from the group consisting of epinephrine, propylhexedrine, and combinations thereof.

5. A chemically impregnated liquid absorbent gingival retraction cord that is resistant to degradation by corrosive agents, comprising:
   a liquid absorbent knitted retraction cord formed from one or more blended strands, the one or more blended strands being formed into a knit of a plurality of interlocking loops so as to form the knitted retraction cord and so as to be deformable and liquid absorbent, wherein each of the one or more blended strands comprises:
      at least one degradation resistant silk strand, and
      at least one degradable natural fiber strand,
      the at least one degradation resistant silk strand and the at least one degradable natural fiber strand being twisted together into the one or more blended strands that are formed into the knit of the plurality of interlocking loops, the one or more blended strands each comprising a blend of materials composed of at least 50% silk; and
   a corrosive active agent impregnated within the liquid absorbent knitted retraction cord which degrades the at least one degradable natural fiber strand while the at least one degradation resistant silk strand resists degradation by the corrosive active agent such that the knitted retraction cord is enabled to maintain overall structural integrity of the knit without degradation of the at least one silk strand by the corrosive active agent.

6. A chemically impregnated liquid absorbent gingival retraction cord as defined in claim 5, wherein the at least one degradable natural fiber strand comprises cotton.

7. A chemically impregnated liquid absorbent gingival retraction cord as defined in claim 5, wherein at least one of the blended strands further comprises nylon and/or polyester.

8. A chemically impregnated liquid absorbent gingival retraction cord as defined in claim 5, wherein the retraction cord is substantially free of synthetic degradation resistant fibers.

9. A chemically impregnated liquid absorbent gingival retraction cord as defined in claim 5, wherein the corrosive active agent is a hemostat selected from the group consisting of potassium aluminum sulfate, aluminum ammonium sulfate, aluminum sulfate, aluminum chlorohydrate, aluminum acetate, aluminum chloride, ferric sulfate, ferric subsulfate, ferric chloride, permanganates, tannins, zinc chloride, and combinations thereof.

10. A chemically impregnated liquid absorbent gingival retraction cord as defined in claim 5, further comprising a vasoconstrictor selected from the group consisting of epinephrine, propylhexedrine, and combinations thereof.

11. A chemically impregnated liquid absorbent gingival retraction cord as defined in claim 5, wherein each of the one or more blended strands comprises at least about 80% silk.

12. A chemically impregnated liquid absorbent gingival retraction cord as defined in claim 5, wherein each of the one or more blended strands comprises at least about 90% silk.

13. A chemically impregnated liquid absorbent gingival retraction cord as defined in claim 5, wherein each of the one or more blended strands comprises at least about 95% silk.

14. A liquid absorbent gingival retraction cord that can be impregnated with a corrosive active agent yet be resistant to degradation by corrosive agents, comprising:
   a plurality of strands being formed into a plurality of interlocking loops so as to form a knitted retraction cord that is deformable and liquid absorbent; and wherein the liquid absorbent gingival retraction cord consists essentially of silk so as to be resistant to degradation by corrosive agents applied to the retraction cord.

15. A chemically impregnated liquid absorbent gingival retraction cord that is resistant to degradation by corrosive agents, comprising:
- a liquid absorbent knitted retraction cord formed from one or more strands consisting essentially of silk and optionally one or more strands comprised of a material other than or in addition to silk, the one or more strands consisting essentially of silk being formed into a knit of a plurality of interlocking loops so as to form the knitted retraction cord and so as to be deformable and liquid absorbent, wherein the retraction cord is comprised of silk and; and
- a corrosive active agent impregnated within the liquid absorbent knitted retraction cord,
- wherein the knitted retraction cord is both liquid absorbent and resists degradation by the corrosive active agent.

* * * * *